US009162009B2

(12) United States Patent
Rapsey et al.

(10) Patent No.: US 9,162,009 B2
(45) Date of Patent: Oct. 20, 2015

(54) DRUG DELIVERY USING A SACRIFICIAL HOST

(71) Applicant: Cochlear Limited, Macquarie University, NSW (AU)

(72) Inventors: Jane Rapsey, Berowra (AU); Martin Svehla, Botany (AU); Peter Schuller, Turramurra (AU); Christopher Robert Miller, Dulwich Hill (AU)

(73) Assignee: Cochlear Limited, Macquarie University, NSW (AU)

( * ) Notice: Subject to any disclaimer, the term of this patent is extended or adjusted under 35 U.S.C. 154(b) by 0 days.

(21) Appl. No.: 14/064,354

(22) Filed: Oct. 28, 2013

(65) Prior Publication Data
US 2014/0188033 A1    Jul. 3, 2014

Related U.S. Application Data

(63) Continuation of application No. 13/355,133, filed on Jan. 20, 2012, now abandoned.

(51) Int. Cl.
*A61N 1/00*      (2006.01)
*A61L 27/20*    (2006.01)
(Continued)

(52) U.S. Cl.
CPC .............. *A61L 27/20* (2013.01); *A61L 27/18* (2013.01); *A61L 27/54* (2013.01); *A61L 27/58* (2013.01);
(Continued)

(58) Field of Classification Search
CPC .............. A61L 27/18; A61L 2300/602; A61L 2430/14; A61L 27/20; A61L 27/54; A61L 27/58; C08L 83/04; A61F 11/00; A61F 2250/0067; A61N 1/0541; A61N 1/36032

USPC ...................................................... 607/3, 137
See application file for complete search history.

(56) References Cited

U.S. PATENT DOCUMENTS

| 4,351,337 A | 9/1982 | Sidman |
| 5,648,097 A * | 7/1997 | Nuwayser ..................... 424/489 |

(Continued)

FOREIGN PATENT DOCUMENTS

| WO | 2002041666 A1 | 5/2002 |
| WO | 2004050056 A1 | 6/2004 |
| WO | 2009029866 A2 | 3/2009 |

OTHER PUBLICATIONS

Examination Report in Australian Patent Application No. 2013202771, issued Oct. 31, 2014, 7 pages.
(Continued)

*Primary Examiner* — George Manuel

(57) ABSTRACT

Implantable drug-doped component, e.g., a cochlear implant, including host material, a host-embedded drug, a sacrificial material integrated with the host. Sacrificial material facilitates release of drug from the component. Sacrificial material facilitates release through creation of voids in the host upon dissolution of sacrificial material upon contact with a solvent, e.g., perilymph fluid upon implant. Host can be polysiloxane, or silicone rubber. Drug can be anti-inflammatory, growth factor, antibody, anti-oxidant, antibiotic, corticosteroid. Sacrificial material can be: glucose monomer, sugar, cyclodextrin, dissolvable or resorbable at implant site, a salt, bioresorbable material, hyaluronic acid, polyurethane, polyester, polyamide, polyvinyl alcohol, polyacrylic acid. Sacrificial material can be the host, and can facilitate release of drug through changing a property of sacrificial material, e.g., by exposing component to ethanol wash. For a cochlear implant, drug doped material can be applied to a non-stimulating surface of the electrode array, and can be a physical feature of stimulating medical device, e.g., soft tip, ridge, spine. For a cochlear implant the drug-doped material can excluded from the basal side of the most basal electrode contact.

34 Claims, 8 Drawing Sheets

(51) Int. Cl.
*A61N 1/05* (2006.01)
*A61L 27/18* (2006.01)
*A61L 27/54* (2006.01)
*A61L 27/58* (2006.01)
*A61N 1/36* (2006.01)
*A61F 11/00* (2006.01)

(52) U.S. Cl.
CPC .......... *A61N 1/0541* (2013.01); *A61N 1/36032* (2013.01); *A61F 11/00* (2013.01); *A61F 2250/0067* (2013.01); *A61L 2300/602* (2013.01); *A61L 2430/14* (2013.01)

(56) References Cited

U.S. PATENT DOCUMENTS

| | | | | |
|---|---|---|---|---|
| 8,283,569 | B2* | 10/2012 | Johnson et al. | 174/255 |
| 8,673,336 | B2* | 3/2014 | Parker et al. | 424/423 |
| 2004/0241204 | A1 | 12/2004 | Martinod et al. | |
| 2006/0073182 | A1* | 4/2006 | Wong et al. | 424/426 |
| 2006/0287689 | A1 | 12/2006 | Debruyne et al. | |
| 2007/0173787 | A1* | 7/2007 | Huang et al. | 604/891.1 |
| 2007/0213799 | A1* | 9/2007 | Jolly et al. | 607/137 |
| 2009/0012594 | A1 | 1/2009 | Gibson | |
| 2009/0076581 | A1 | 3/2009 | Gibson | |
| 2010/0106134 | A1* | 4/2010 | Jolly et al. | 604/506 |
| 2011/0172763 | A1* | 7/2011 | Ndondo-Lay | 623/1.42 |
| 2011/0288500 | A1 | 11/2011 | Dadd et al. | |

OTHER PUBLICATIONS

International Preliminary Report on Patentability in International Application No. PCT/IB2013/050493, mailed Jul. 22, 2014, 7 pages.
International Search Report and Written Opinion in International Application No. PCT/IB2013/050493, mailed Jun. 25, 2013, 11 pages.
Farahmand Ghavi, et al., "Corticosteroid-releasing cochlear implant: A novel hybrid of biomaterial and drug delivery system," Journal of Biomedical Materials Research B: Applied Biomaterials, Aug. 2010, vol. 94B, Issue 2, pp. 388-398.

* cited by examiner

FIG. 4
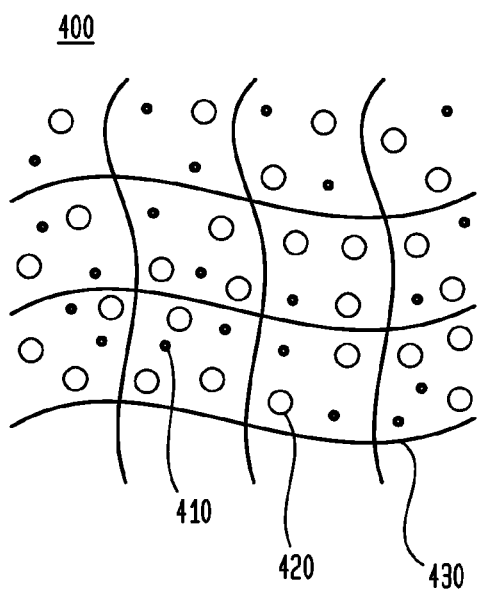
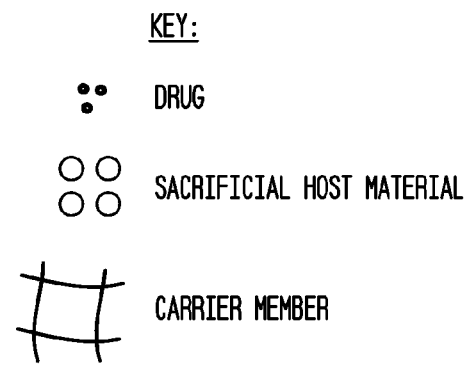

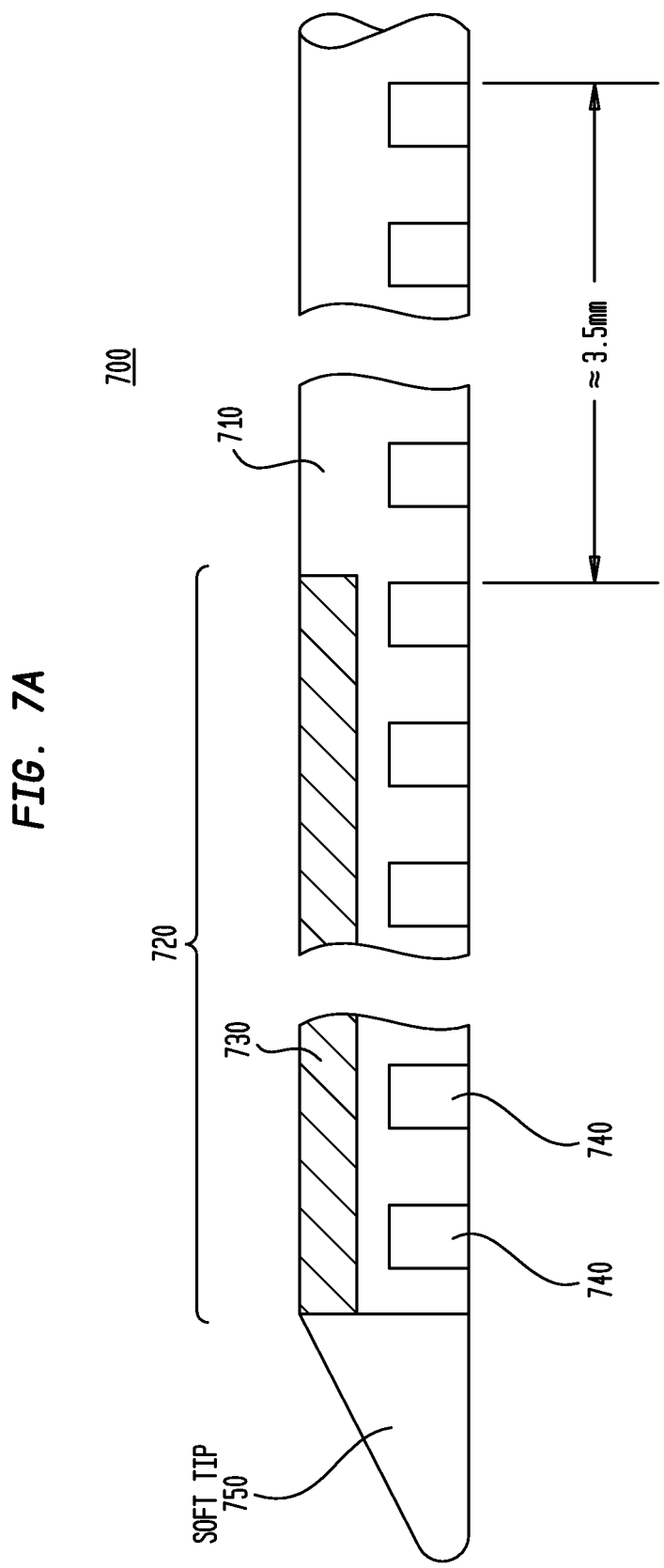

DRUG DELIVERY USING A SACRIFICIAL HOST

CROSS-REFERENCE TO RELATED APPLICATIONS

This application is a Continuation Application of U.S. patent application Ser. No. 13/355,133, filed Jan. 20, 2012.

FIELD

The disclosed technology relates to implantable medical devices, and in particular to implantable medical devices used to deliver drugs.

BACKGROUND

Implantable medical devices are capable of providing a wide range of benefits to a patient. Traditionally, there has been interest in delivering bioactive substances or chemicals (generally and collectively referred to herein as "drugs") in conjunction with such medical devices for a variety of purposes. For example, in one conventional approach the implantable medical device is coated with a bioactive substance. In other conventional approaches various techniques for delivering drugs in liquid form to a target location in a patient from an external or implanted reservoir.

In many conventional approaches, a bioactive substance is integrated into the polymeric coating of the implantable medical device or accompanying component. These and other conventional approaches typically require the incorporation of the drug into the implantable medical device during the manufacturing process of the device. This requirement introduces a number of difficult problems and challenges for the manufacturing and sterilization processes. On the other hand, the use of reservoirs provides significant limitations to many aspects of the administration of the drug therapy.

SUMMARY

The technology includes an implantable drug-doped component, e.g., a cochlear implant, that includes a host material, a drug embedded in the host material, and a sacrificial material integrated with the host material. The sacrificial material facilitates the release of the embedded drug from the drug-doped component. The sacrificial material can facilitate the release of the drug from the drug-doped component through the creation of voids in the host material upon dissolution of the sacrificial material upon contact with a solvent. The contact with a solvent can be upon implant of the component in a recipient, e.g., perilymph as the solvent. The host material can be one or more of a polysiloxane and a silicone rubber. The drug can be one or more of an anti-inflammatory, a growth factor, an antibody, an anti-oxidant, an antibiotic, and a corticosteroid. The sacrificial material can be one or more of: a glucose monomer, a sugar, cyclodextrin, a material that is at least one of dissolvable and re-sorbable in the environment of an implant site, a salt, a bioresorbable material, hyaluronic acid, polyurethane, polyester, polyamide, polyvinyl alcohol, and polyacrylic acid. In some embodiments, the sacrificial material is the host material, and the sacrificial material facilitates the release of the drug from the drug-doped component through changing a property of the sacrificial material. The change in property can be brought about by exposing the drug-doped component to an ethanol wash. For a cochlear implant comprising a drug-doped component, the drug doped material can be applied to a non-stimulating surface of the electrode array of the cochlear implant. The drug doped material can be a physical feature of the stimulating medical device, such as a soft tip, a ridge, or a spine.

DESCRIPTION OF THE DRAWINGS

Embodiments of the disclosed technology are described below with reference to the attached drawings, in which:

FIG. 4 is a schematic representation of a set of relationships between a carrier member, a drug, and a sacrificial material in accordance with embodiments of the present technology;

FIG. 7A is a view of a section of an electrode assembly with drug-doped material extending down the lateral non-stimulating surface of the carrier member, in accordance with embodiments of the present technology.

DETAILED DESCRIPTION

Embodiments are described herein primarily in connection with one type of implantable medical device, a hearing prosthesis, and more specifically a cochlear implant. Cochlear implants are hearing prostheses that deliver electrical stimulation, alone or in combination with other types of stimulation, to the cochlear of a recipient. Therefore, as used herein a cochlear implant refers to a device that delivers electrical stimulation in combination with other types of stimulation, such as acoustic and/or mechanical stimulation.

It would be appreciated that embodiments of the present technology can be implemented in any cochlear implant or other hearing prosthesis now know or later developed; including auditory brain stimulators (also known as auditory brainstem implants (ABIs)). Furthermore, it would be understood that embodiments of the present technology can be implemented in implantable medical devices other than cochlear implants such as neurostimulators, cardiac pacemakers/defibrillators, functional electrical stimulators (FES), spinal cord stimulators (SCS), etc.

Figure 1:
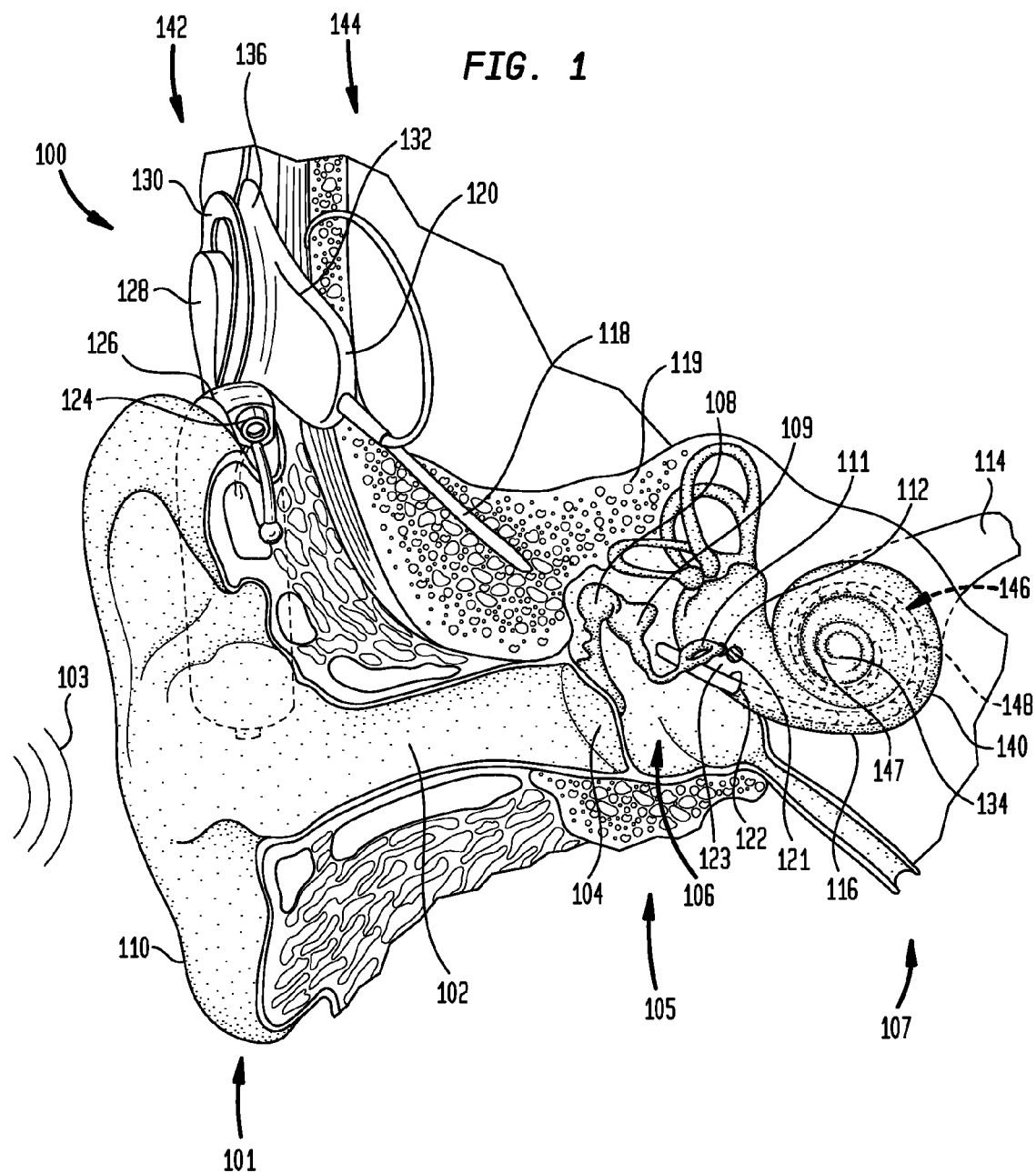
FIG. 1 is a perspective view of an exemplary stimulating medical device, a cochlear implant, having an electrode assembly in accordance with embodiments of the present technology.

FIG. 1 is a perspective view of an exemplary cochlear implant 100 implanted in a recipient having an outer ear 101, a middle ear 105, and an inner ear 107. Components of outer ear 101, middle ear 105, and inner ear 107 are described below, followed by a description of cochlear implant 100.

In a fully functional ear, outer ear 101 comprises an auricle 110 and an ear canal 102. An acoustic pressure or sound wave 103 is collected by auricle 110 and channeled into and through ear canal 102. Disposed across the distal end of ear cannel 102 is a tympanic membrane 104 that vibrates in response to sound wave 103. This vibration is coupled to oval window or fenestra ovalis 112 through three bones of middle ear 105, collectively referred to as the ossicles 106 and comprising the malleus 108, the incus 109, and the stapes 111.

Bones 108, 109, and 111 of middle ear 105 serve to filter and amplify sound wave 103, causing oval window 112 to articulate, or vibrate, in response to vibration of tympanic membrane 104. This vibration sets up waves of fluid motion of the perilymph within cochlea 140. Such fluid motion, in turn, activates tiny hair cells (not shown) inside of cochlea 140. Activation of the hair cells causes appropriate nerve impulses to be generated and transferred through the spiral ganglion cells (not shown) and auditory nerve 114 to the brain (also not shown) where they are perceived as sound.

Cochlear implant 100 comprises an external component 142 that is directly or indirectly attached to the body of the recipient, and an internal or implantable component 144 that is temporarily or permanently implanted in the recipient. External component 142 typically comprises one or more sound input elements, such as microphone 124 for detecting sound, a sound processing unit 126, a power source (not shown), and an external transmitter unit 128. External transmitter unit 128 comprises an external coil 130, and preferably, a magnet (not shown) secured directly or indirectly to external coil 130. Sound processing unit 126 processes the output of microphone 124 that is positioned, in the depicted embodiment, by auricle 110 of the recipient. Sound processing unit 126 generates encoded signals, sometimes referred to herein as encoded data signals, which are provided to external transmitter unit 128 via a cable (not shown).

Internal component 144 comprises an internal receiver unit 132, a stimulator unit 120, and an elongate stimulating lead assembly 118. Internal receiver unit 132 comprises an internal coil 136, and preferably, a magnet (also not shown) fixed relative to the internal coil. Internal receiver unit 132 and stimulator unit 120 are hermetically sealed within a biocompatible housing, sometimes collectively referred to as a stimulator/receiver unit. Internal coil 136 receives power and stimulation data from external coil 130, as noted above. Elongate stimulating lead assembly 118 has a proximal end connected to stimulator unit 120, and extends through mastoid bone 119. Lead assembly 118 has a distal region, referred to as electrode assembly 145, implanted in cochlea 140. As used herein the term "stimulating lead assembly," refers to any device capable of providing stimulation to a recipient, such as, for example, electrical or optical stimulation.

Electrode assembly 145 may be implanted at least in basal region 116 of cochlea 140, and sometimes further. For example, electrode assembly 145 may extend towards apical end of cochlea 140, referred to as cochlea apex 134. Electrode assembly 145 may be inserted into cochlea 140 via a cochleostomy 122, or through round window 121, oval window 112, and the promontory 123 or opening in an apical turn 147 of cochlea 140.

Electrode assembly 145 has disposed therein or thereon a longitudinally aligned and distally extending array 146 of electrode contacts 148, sometimes referred to as electrode array 146 herein. Throughout this description, the term "electrode array" means a collection of two or more electrode contacts, sometimes referred to simply as contacts herein. As used herein, electrode contacts or other elements disposed in a carrier refer to elements integrated in, positioned on, or generally attached to the carrier member. As such, electrode array 146 is referred to herein as being disposed in electrode assembly 145. Stimulator unit 120 generates stimulation signals which are applied by electrodes 148 to cochlea 140, thereby stimulating auditory nerve 114.

In cochlear implant 100, external coil 130 transmits electrical signals (i.e., power and stimulation data) to internal coil 136 via a radio frequency (RF) link. Internal coil 136 is typically a wire antenna coil comprised of multiple turns of electrically insulated single-strand or multistrand platinum or gold wire. The electrical insulation of internal coil 136 is provided by a flexible silicone molding (not shown). In use, implantable receiver unit 132 may be positioned in a recess of the temporal bone adjacent auricle 110 of the recipient.

As noted, FIG. 1 illustrates a context of the present technology in which cochlear implant 100 includes an external component 142. It would be appreciated that in alternative embodiments, cochlear implant 100 comprises a totally implantable prosthesis that is capable of operating, at least for a period of time, without the need of an external component. In such embodiments, all components of cochlear implant 100 are implantable, and the cochlear implant operates in conjunction with external component 142.

Figure 2:
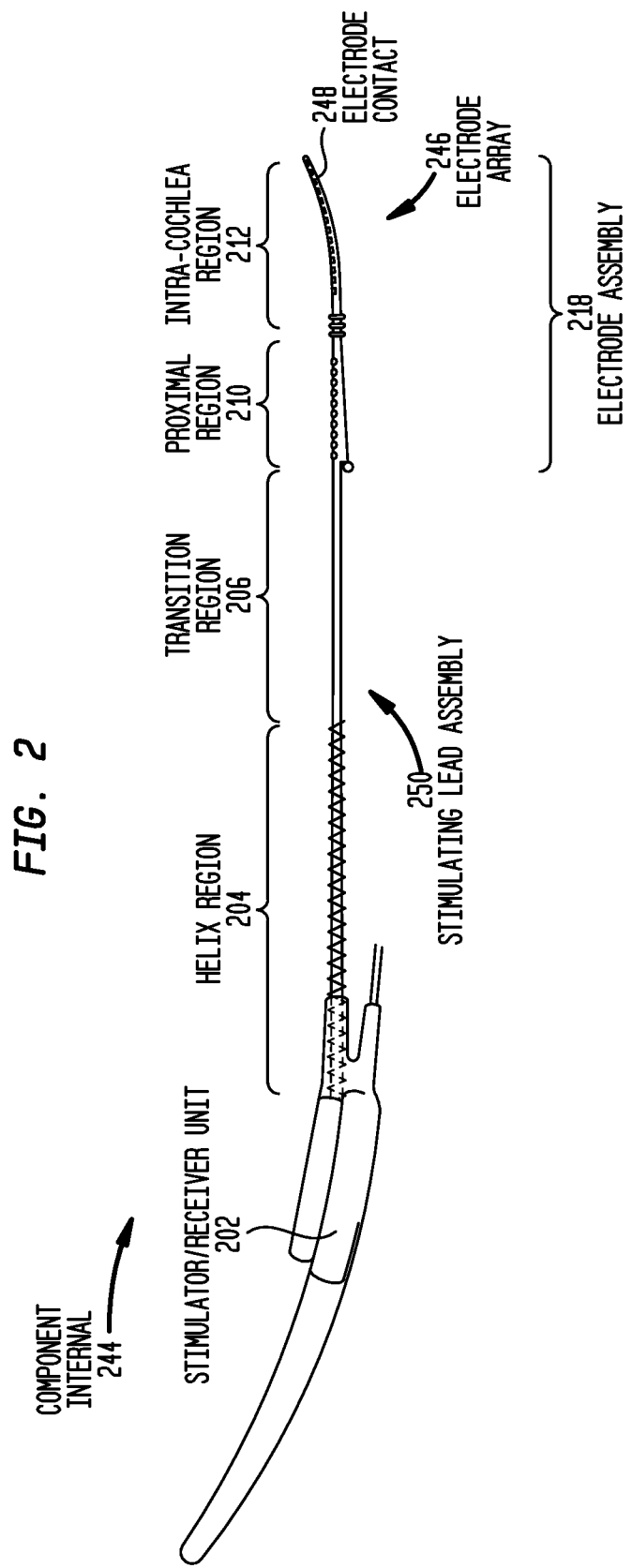
FIG. 2 is a side view of a conventional implantable component of a cochlear implant.

FIG. 2 is a simplified side view of an embodiment of internal component 144, referred to herein as internal component 244. As shown in FIG. 2, internal component 244 comprises a stimulator/receiver unit 202, which, as described above, receives encoded signals from an external component of the cochlear implant. Connected to stimulator/receiver unit 202 is a stimulating lead assembly 250. Stimulating lead assembly 250 terminates in an electrode assembly 218 that comprises a proximal region 210 and an intra-cochlear region 212. Intra-cochlear region 212 is configured to be implanted in the recipient's cochlea and has disposed thereon an array 246 of electrode contacts 248. Proximal region 210 is configured to be positioned outside of the recipient's cochlea.

In certain embodiments, electrode assembly 218 is configured to adopt a curved configuration during or after implantation into the recipient's cochlea. To achieve this, in certain embodiments, electrode assembly 218 is pre-curved to the same general curvature of a cochlea. In such embodiments, electrode assembly 218 is referred to as perimodiolar electrode assembly that is held straight by, for example, a stiffening stylet (not shown), which stylet is removed during implantation so that the electrode assembly may adopt its curved configuration when in the cochlea. Other methods of implantation, as well as other electrode assemblies that adopt a curved configuration, may be used in embodiments of the present technology.

In other embodiments, electrode assembly 218 is a non-perimodiolar electrode assembly that does not adopt a curved configuration. For example, electrode assembly 218 may comprise a straight electrode assembly or a mid-scala assembly that assumes a mid-scala position during or following implantation.

In the illustrative embodiments of FIG. 2, stimulating lead assembly 250 further comprises a helix region 204 and a transition region 206 connecting stimulator/receiver unit 202 to electrode assembly 218. Helix region 204 prevents the connection between stimulator/receiver 202 and electrode assembly 218 from being damaged due to movement of internal component 244 which may occur, for example, during mastication.

There have been a number of proposals for delivering drugs to an implant site. Successful delivery of drugs to an implant site can provide benefits such as: faster recovery at the implant trauma, an increase in stimulation effectiveness (e.g., by supporting hair cell survival and growth in cochlear implants), directly targeting diseases such as tinnitus, promoting acceptance of the implant at the site, and facilitating the function of the implant. Drug delivery to a cochlear implant site can be achieved, inter alia, through embedding a portion of the implant, e.g., the electrode assembly, with the drug. As used herein, the term "drug" includes, but is not limited to, therapeutic, prophylactic, and diagnostic agents.

Many implants, e.g., cochlear implants, employ structural elements that are intended to remain in a recipient for the long term. As such, these structural elements are typically more hydrophobic than not, and are required to maintain structural integrity over the long term. For example, silicone rubber, typically used as a structural element in such devices, is hydrophobic in nature, and this is a significant impediment to complete drug release in the short term from a silicone rubber/drug mix. In particular, short-term (e.g., 29 days or less) drug delivery from devices intended to implanted for the long term has proved challenging.

Embodiments of the present technology employ a sacrificial material with a drug, in combination with a host material (e.g., the carrier member 310 of the electrode assembly, or at least a portion of the outer layer of the receiver/stimulator unit) to form a drug doped material. Using the combination of the sacrificial material, drug, and host material can modify the characteristics of the aggregate material (e.g., the carrier member 310) and enhance drug bioavailability.

Figure 3:
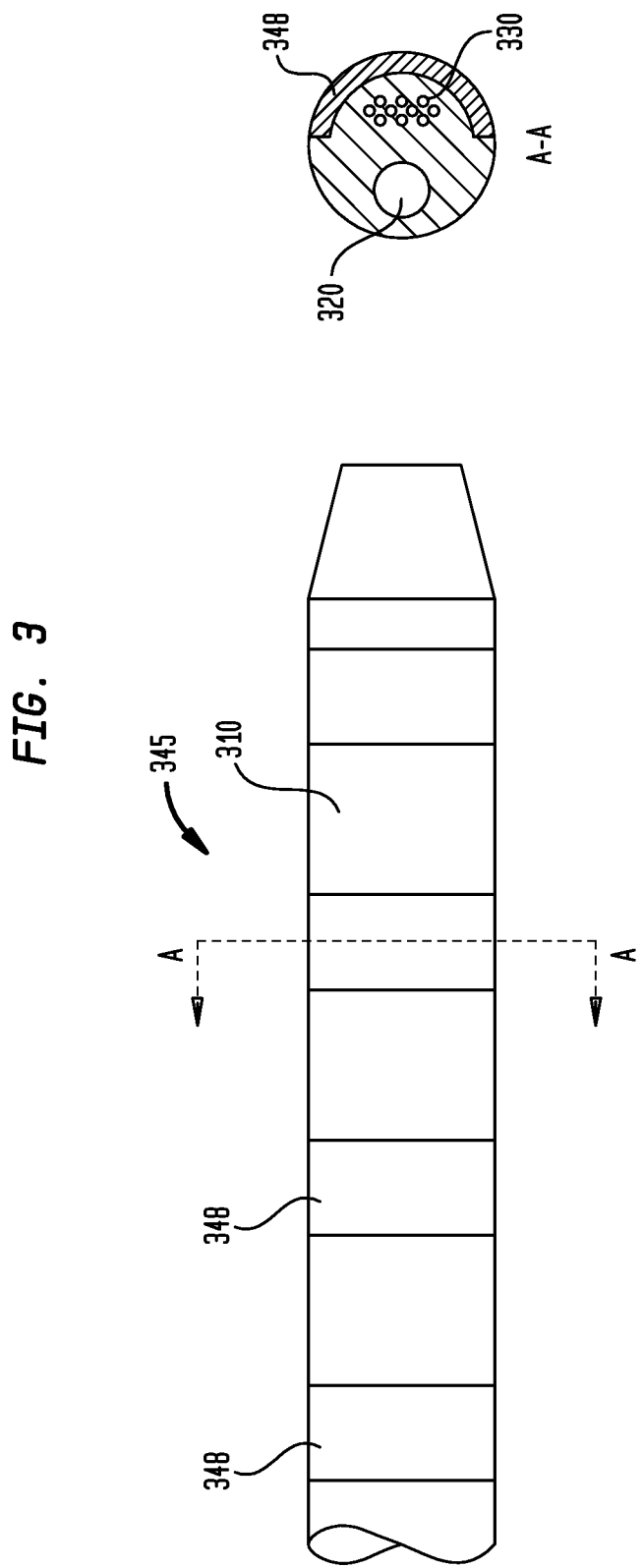
FIG. 3 is a side view and a cross section view of a section of an electrode assembly.

FIG. 3 shows an end section of a typical electrode assembly 345 comprising an elongate electrode carrier member 310 having a plurality of electrode contacts 348 mounted thereon. This particular electrode assembly 345 defines a lumen 320 (shown in cross-section A-A) that, prior to insertion of the assembly 345 into the cochlea, can receive a substantially straight stylet. Such a stylet typically has a stiffness that is sufficient to retain the assembly 345 in a straight configuration. Other electrode assemblies may be used in embodiments of the present technology. Conductive pathways 330 are shown in the cross section of the electrode assembly 345. Each conductive pathway 330 is typically connected to a contact 348.

The carrier member 310 is a structural element of the electrode assembly 345, and is typically made from a hydrophobic material such as medical grade silicone. The carrier member 310 can be made from any number of polysiloxanes, for example, silicone rubber Med 4860 available from Nusil.

Some embodiments of the technology are referred to herein as "void-creating" embodiments.

Referring to FIG. 4, in some void-creating embodiments 400 of the technology, the drug 410 and a sacrificial material 420 are combined and added to the host material 430 of the carrier member 310. Elution of the drug through the host material 430 is facilitated by voids in host material 430 created when the sacrificial material has been sacrificed, e.g., by exposure to one or more of a solvent, eluent, heat, or electromagnetic field. Voids decrease the time required for a sufficient proportion of the drug to enter the body surrounding the implant with less drug residue remaining in the electrode assembly, therefore increasing the amount of drug available for its intended purpose.

In some void-creating embodiments, the sacrificial material can be a glucose monomer, or sugar, e.g., cyclodextrins, sometimes called cycloamyloses, that are produced from starch by means of enzymatic conversion. Such materials are used in food, pharmaceutical, and chemical industries, as well as agriculture and environmental engineering. The sacrificial material can be any number of natural or synthetic agents which dissolve or re-sorb, including but not limited to salts. The sacrificial material also can be a bioresorbable material such as hyaluronic acid, polyvinyl alcohol (PVA), poly acrylic acid (PAA), polyurethanes, polyesters, polyamides among others.

Figure 5:
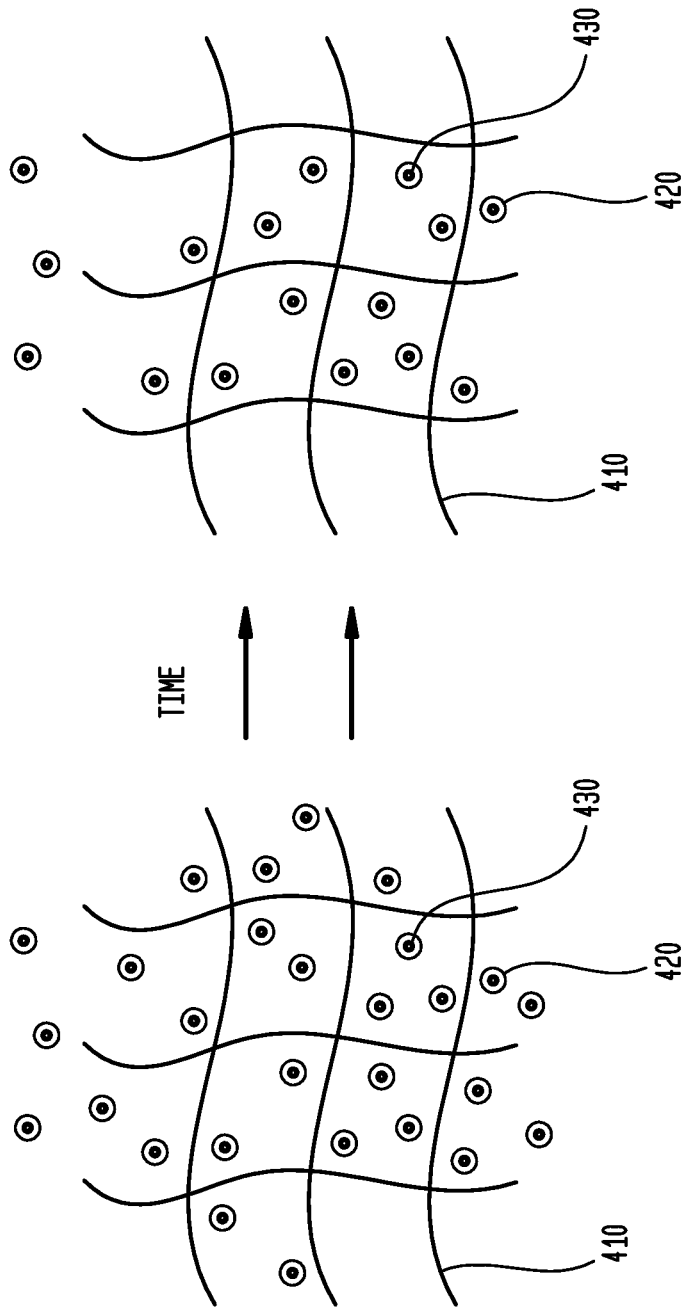
FIG. 5 is a schematic representation of a set of relationships between a carrier member, a drug, and a sacrificial material in accordance with embodiments of the present technology.

Referring to FIG. 5, in some void-creating embodiments 400 of the technology, the drug 430 can be coated in the sacrificial material 420 and elution can occur by the drug 430 leaving the host material 430 as the sacrificial material 420 dissolves.

Without being bound by theory, it is believed that combining the drug with a sacrificial material in the largely hydrophobic carrier body allows the drug to elute through the carrier body in less time than it otherwise would based at least in part on voids created when the sacrificial material leaves the bulk material.

In some embodiments of the technology, referred to herein as "wash" embodiments, the drug-doped material is exposed, e.g., via dipping or through a wash, to a substance that improves the drug doped material's ability to release the drug. Without being bound by theory, it is believed that washing a drug-doped component in a wash such as those described herein, allows the drug to elute through the drug-doped material in less time than it otherwise would, based on the wash breaking oligomers of the host material.

In some wash embodiments of the technology, a drug-dope device (or at least the regions of the device carry the drug) is dipped in a wash, e.g., an ethanol wash, for a suitable period of time. This step can be performed during manufacturing, soon after manufacture of the device, or just prior to insertion of the device.

In some embodiments of the technology, the area of drug application is limited. Limiting the area of application of the drug doped material can assist in maintaining the integrity of the carrier member 410 after release of the drug has taken place. It is likely that after release of the drug from the drug doped material, voids would be left within the bulk material of the carrier member. These voids could result in negative effects, for example, allow for an ionic path for fluids to access the conductive pathway insulation and joins of conducting pathways to stimulating contacts. The voids may also impact upon the bulk material acting as a retention mechanism for the stimulating contacts within the carrier member 410. The voids could also cause delaminating of bulk material layers during a multiple molding processes. Limiting the area of application for the drug doped material would avoid these issues.

Figure 7B:
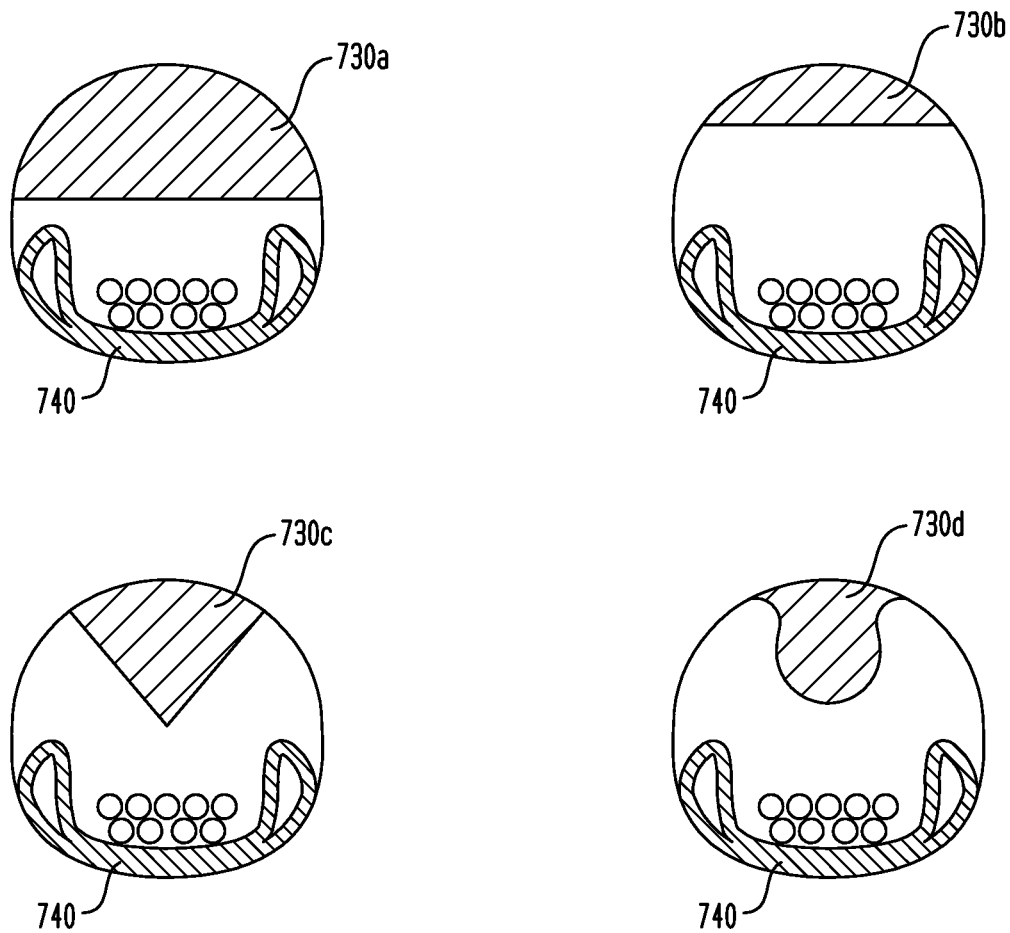
FIG. 7B illustrates exemplary cross sections of a spine of FIG. 7A, in accordance with embodiments of the present technology.

Referring to FIG. 7A, a section 700 of an electrode assembly with the drug-doped material extending down the lateral non-stimulating surface (surface 720) of the carrier member 710 away from the contacts 740, for example, in the form of a spine 730. The drug-doped material also may exist as a feature of the carrier member 710, for example, in the form of a soft tip 750, among others. FIG. 7B illustrates exemplary cross sections of such a spine 730a, 730b, 730c, and 730d.

The drug can be an anti-inflammatory such as Dexamethasone. Other drugs that could be applied using this technique could include growth factors, antibodies, anti-oxidants, anti-inflammatory, antibiotics, corticosteroid etc, as applicable.

Figure 6:
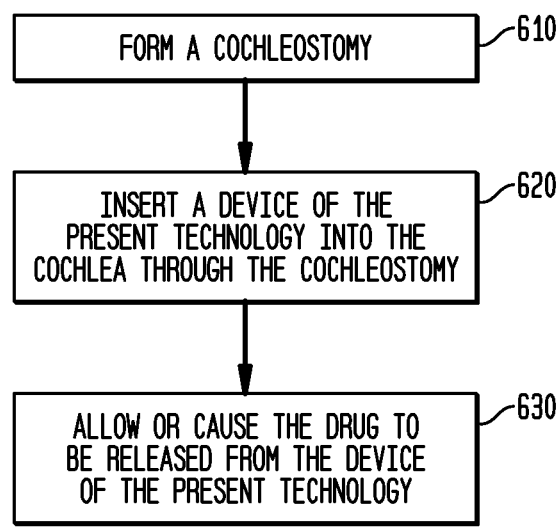
FIG. 6 is a flowchart of methods in accordance with embodiments of the present technology.

The technology includes methods of delivering a drug to an implant site. As an exemplary method, consider delivery of a drug to the implant site of a cochlear implant electrode assembly using any one of the devices described herein. In such method, as illustrated in FIG. 6, a cochleostomy is formed 610. The device (as described above to contain the drug) is inserted through the cochleostomy 620. The drug is one or both of allowed and caused to be released from the drug-doped electrode assembly 630. Methods for allowing or causing the drug to be released from the drug-doped assembly containing sacrificial material include exposing the one or more of: a solvent or eluent such as perilymph fluid; heat (such as the recipient's body heat); an electromagnetic field; and a vibration, sonic, or ultrasound force.

While various embodiments of the present invention have been described above, it should be understood that they have been presented by way of example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the following claims and their equivalents. All patents and publications discussed herein are incorporated in their entirety by reference thereto.

What is claimed is:

1. An implantable drug-doped component comprising:
   a hydrophobic carrier material,
   a drug embedded in the carrier material, and
   a sacrificial host material integrated with the carrier material;
   wherein upon implantation of the drug-doped component into a recipient, the sacrificial host material is configured to dissolve to create voids in the carrier material that facilitate the release of the embedded drug from the carrier material.

2. The implantable drug-doped component of claim 1, wherein the sacrificial host material is configured to dissolve following contact with perilymph fluid of the recipient.

3. The implantable drug-doped component of claim 1, wherein the carrier material is a polysiloxane.

4. The implantable drug-doped component of claim 1, wherein the carrier material is a silicone rubber.

5. The implantable drug-doped component of claim 1, wherein the drug is at least one material selected from the group comprising:
   an anti-inflammatory, a growth factor, an antibody, an anti-oxidant, an antibiotic, and a corticosteroid.

6. The implantable drug-doped component of claim 1, wherein the sacrificial host material is at least one of:
   a glucose monomer and a sugar.

7. The implantable drug-doped component of claim 1, wherein the sacrificial host material is a cyclodextrin.

8. The implantable drug-doped component of claim 1, wherein the sacrificial host material is a material that is re-sorbable in the environment of an implant site.

9. The implantable drug-doped component of claim 1, wherein the sacrificial host material is a salt.

10. The implantable drug-doped component of claim 1, wherein the sacrificial host material is a bioresorbable material.

11. The implantable drug-doped component of claim 1, wherein the sacrificial host material is at least one material selected from the group comprising:
    hyaluronic acid, polyurethane, polyester, polyamide, polyvinyl alcohol, and polyacrylic acid.

12. A cochlear implant comprising:
    an electrode array; and
    a drug-doped component configured to be implanted in a recipient, and comprising:
      a hydrophobic carrier material,
      a drug embedded in the carrier material, and
      a sacrificial host material integrated with the carrier material;
    wherein the sacrificial host material is configured to dissolve upon implantation of the drug-doped component into the recipient to create voids in the carrier material that facilitate the release of the embedded drug from the carrier material.

13. The cochlear implant of claim 12 wherein the sacrificial host material is configured to dissolve following contact with a solvent.

14. The cochlear implant of claim 12, wherein the solvent is perilymph fluid.

15. The cochlear implant of claim 12, wherein the carrier material is a polysiloxane.

16. The cochlear implant of claim 12, wherein the carrier material is a silicone rubber.

17. The cochlear implant of 12, wherein the drug is at least one material selected from the group comprising:
    an anti-inflammatory, a growth factor, an antibody, an anti-oxidant, an antibiotic, and a corticosteroid.

18. The cochlear implant of 12, wherein the sacrificial host material is at least one of:
    a glucose monomer and a sugar.

19. The cochlear implant of claim 12, wherein the sacrificial host material is a cyclodextrin.

20. The cochlear implant of claim 12, wherein the sacrificial host material is a material that is re-sorbable in the environment of an implant site.

21. The cochlear implant of claim 12, wherein the sacrificial host material is a salt.

22. The cochlear implant of claim 12, wherein the sacrificial host material is a bioresorbable material.

23. The cochlear implant of claim 12, wherein the sacrificial host material is at least one material from the group comprising:
    Hyaluronic acid, polyurethane, polyester, polyamide, polyvinyl alcohol, and polyacrylic acid.

24. The cochlear implant of claim 12, wherein the drug doped material is disposed at a non-stimulating surface of the electrode array.

25. The cochlear implant of 12, wherein the drug-doped material is a physical feature of the electrode array.

26. The cochlear implant of claim 25, wherein the drug-doped material is at least one physical feature selected from the group of physical features comprising:
    a soft tip, a ridge, and a spine of the electrode array.

27. The cochlear implant of claim 12, wherein electrode array comprises a most basal electrode contact, and wherein the drug-doped material is not applied on the basal side of the most basal electrode contact.

28. An implantable component comprising:
    a non-resorbable carrier material;
    a drug embedded in the carrier material; and
    a sacrificial host material integrated with the carrier material configured to be sacrificed upon implantation into a recipient to form voids in the carrier material facilitating release of the drug from the carrier material.

29. The implantable component of claim 28, wherein the sacrificial host material is at least one of a dissolvable and a re-sorbable material.

30. The implantable component of claim 28, wherein the sacrificial host material is configured to form voids in the carrier material upon exposure to an eluent.

31. The implantable component of claim 28, wherein the sacrificial host material is configured to form voids in the carrier member upon contact with a solvent.

32. The implantable component of claim 31, wherein the sacrificial host material is configured to form voids in the carrier member upon contact with perilymph fluid of the recipient.

33. The implantable component of claim 28, wherein the sacrificial host material is configured to form voids in the carrier member upon exposure to the recipient's body heat.

34. The implantable component of claim 28, wherein the sacrificial host material is configured to form voids in the carrier member upon exposure to an electromagnetic field after implantation of the implantable component in the recipient.

* * * * *